United States Patent [19]

Lathe et al.

[11] Patent Number: 5,744,133
[45] Date of Patent: Apr. 28, 1998

[54] EXPRESSION OF A TUMOR-SPECIFIC ANTIGEN BY A RECOMBINANT VECTOR VIRUS AND USE THEREOF IN PREVENTITIVE OR CURATIVE TREATMENT OF THE CORRESPONDING TUMOR

[75] Inventors: Richard Lathe; Marie-Paule Kieny. both of Strasbourg; Guerrino Meneguzzi, Nice, all of France

[73] Assignee: Transgene S.A., France

[21] Appl. No.: 357,138

[22] Filed: Dec. 15, 1994

Related U.S. Application Data

[63] Continuation of Ser. No. 248,463, May 24, 1994, abandoned, which is a continuation of Ser. No. 126,021, Sep. 24, 1993, abandoned, which is a continuation of Ser. No. 984,242, Dec. 1, 1992, abandoned, which is a continuation of Ser. No. 546,318, Jul. 2, 1990, abandoned, which is a continuation-in-part of Ser. No. 84,852, Aug. 13, 1987, abandoned.

[30] Foreign Application Priority Data

Aug. 13, 1986 [FR] France .................................. 86 11700
Mar. 6, 1989 [FR] France .................................. 89 02897

[51] Int. Cl.$^6$ .......................... A01N 63/00; C12N 15/86; C12N 7/01; C12N 7/04
[52] U.S. Cl. .................. 424/93.2; 424/93.6; 435/235.1; 435/320.1
[58] Field of Search .......................... 435/320.1, 235.1; 424/93.2, 93.6

[56] References Cited

U.S. PATENT DOCUMENTS 4,603,112  7/1986  Paoletti et al. .......................... 435/235

OTHER PUBLICATIONS

Cason et al. "Toward Vaccines Against Human Papillmavirus type–16 Genital Infections" Vaccine 11(6): 603–611 1993.

Rassoulzadegan et al., The roles of individual polyoma virus early proteins in oncogenic transformation, Nature, vol. 300, 23/30 Dec. 1982, pp. 713–718.

Tyndall et al., A region of the polyoma virus genome between the replication origin and late protein coding sequences is required in cis for both early gene expression and viral DNA replication, Nucleic Acids Research, vol. 9, No. 23, 1981, pp. 6231–6251.

Food and Drug Administration, HHS, 21 CFR Sections 620.1–620.33.

Treisman et al., Transformation of rat cells by an altered polyoma virus genome expressing only the middle–T protein, Nature, vol. 292, Aug. 13, 1981, pp. 595–600.

Primary Examiner—Nancy Degen
Attorney, Agent, or Firm—Cushman Darby & Cushman IP Group of Pillsbury Madison & Sutro LLP

[57] ABSTRACT

The invention concerns a vector being vaccinia virus, which comprises a heterologous DNA sequence which codes at least for the essential region of a tumor specific protein called T antigen, cloned within a non essential region of the vaccinia virus, as well as regulatory element required for the expression of said DNA sequence in higher cells, the vector is particularly useful as a pharmaceutical composition having a preventive or creative activity against tumors especially tumors caused by a papillomavirus.

26 Claims, 10 Drawing Sheets

Scatter plot — Y-axis: DAYS (0 to 100); X-axis categories: VVO, VVbE1, VVbE2, VVbE5, VVbE6, VVbE7

FIG. 6

Scatter plot — Y-axis: DAYS (0, break, 80 to 140); X-axis categories: VO, VVbE5, VVbE6, VVbE7, VVbE5 VVbE6, VVbE6 VVbE7

FIG. 9

```
ATGACAAATCTTGATACTGCATCCACAACATTACTGGGCGTGCTTTTTGCT
1                                                 50
TTGCTTTTGTGTGGCTTTTTGTGTGTCTGCCTATAATACGTCCGCTGCTTT
                                                 100
TGTCTGTGTCTACATACACATCATTAATACTATTGGTATTACTATTGTGG
                                                 150
ATAACAGCAGCCCTCTGCGTTTAGGTGTGTTTTATTGTATATATTGTATTTGT
                                                 200
TTATATACCATTATTTTTAATACATACACATGCACGCTTTTTAATTACATAA
                                                 250
```

EXPRESSION OF A TUMOR-SPECIFIC ANTIGEN BY A RECOMBINANT VECTOR VIRUS AND USE THEREOF IN PREVENTITIVE OR CURATIVE TREATMENT OF THE CORRESPONDING TUMOR

This is a continuation of application Ser. No. 08/248,463, filed on May 24, 1994, which was abandoned upon the filing hereof which is a continuation of application Ser. No. 08/126,021, filed on Sep. 24, 1993, which is a continuation of application Ser. No. 07/984,242, filed Dec. 1, 1992 which is a continuation of application Ser. No. 07/546,318, filed Jul. 2, 1990 which is a continuation in part of application Ser. No. 7/084,852, filed Aug. 13, 1987 all abandoned.

The present invention relates to new recombinant vaccinia viruses and their use as preventive or curative agents useful against tumors, especially tumors induced by papillomaviruses and more especially against human papillomaviruses types HPV-16, HPV-18, HPV-31, HPV-33, HPV-35, HPV-39 and HPV-45.

Tumor cells, whether they are spontaneous or induced by viruses, may have new antigens on their surface (Hellstrom, K. E., Hellstrom, I. & Brown, J. P., Springer Semin. Immunopathol. 5, 127–146, 1982). Tumor-specific antigens (T antigens) have already been used for diagnosing (Herlyn, M., Blaszczyk, M. & Koprowski, H., Contr. Oncol. 19, 160–170, 1984) and visualizing (Begent, R. H. J. Biochim. Biophys. Acta 780, 151–166, 1985) human carcinomas.

More recently, their use as targets in a specific antitumor therapy has been envisaged. The administration of anti-T antibodies, either in the free form or bound to toxins or to radioactive isotopes, has already given encouraging results in the treatment of some clinical cases (Miller, R. A., Maloney, D., Warnke, R., McDougall, R., Wood, G., Kawakami, T., Dilley, J., Goris, M. I. & Levi, R., In: Hybrodomas in Cancer Diagnosis and Treatment, Mitchell, M. S. & Oettgen, H. F. (eds), Raven Press, New York, 1982).

Moreover, it is also possible to attempt to stimulate host-specific immune responses against T antigens following different approaches such as inoculating killed cells expressing T antigen (Gross, L., Cancer Res. 3, 326–333, 1943; Foley, E. J., Cancer Res. 13, 835–837, 1953; Prehn, R. T. & Main, J. M., J. Natl. Cancer Inst. 18, 769–778, 1957), inducing anti-idiotypic antibodies directed against the variable region of anti-T immunoglobulins (Lee, V. K., Harriott, T. G., Kuchroo, V. K., Halliday, W. J., Hellstrom, I. & Hellstrom, K. E., Proc. Natl. Acad. Sci., USA 82, 6286–6290, 1985; Herlyn, D., Ross, A. H. & Koprowski, H. Sciences 232, 100–102, 1986) or injecting the T antigen itself (Teventhia, S. S., Flyer, D. C. & Tijan, R., Virology 107, 13–23, 1980). These experiments are limited by the quantity of antigen available and by the fact that the stimulation of a cell type immune response, which is particularly important in antitumor immunity, requires the simultaneous provision of the antigen and the histocompatibility determinants of the host (Zinkernagel, R. M. & Doherty, P. C., Adv. Immunol. 27, 51–177, 1979).

One object of the invention is to provide means for inducing, in vivo, an antitumor immunity.

One further object of the invention is to provide for expression of a T antigen or a significant portion of the latter by a recombinant vaccinia virus, with the view of inducing, in vivo, an antitumor immunity.

The present invention relates to the use of a vaccinia virus as the expression vector for a DNA sequence coding for the essential region of a tumor-specific protein called T antigen.

A tumor-specific protein means an antigen which is specific for a spontaneous tumor and is absent in normal adult tissues, or an antigen coded by an oncogenic virus, the causative agents of the said tumor.

Essential region of the said protein is meant to denote the portion of the protein sequence capable of inducing an antitumor immunity or of inducing a mechanism capable of causing the said tumor to regress.

Examples have been performed with different T antigens, in order to illustrate the wide scope of the invention.

First of all, T antigens which appear on the surface of rat cells transformed by polyoma virus (PY) (Sjorgren, H. O., Hellstrom, I. & Klein, I. Cancer Res. 21, 329–337, 1961; Habel, K. Proc. Soc. Exp. Biol. Med. 106, 722–725, 1961; Ito, Y., Brocklehurst, J. R. & Dulbecco, R., Proc. Natl. Acad. Sci., USA 74, 4666–4670, 1977) have been expressed by a vaccinia virus and shown to be effective against tumors induced by the polyoma virus.

The polyoma virus induces several types of tumors in rodents. Tumor induction involves the integration of the viral DNA into the host genome and the expression of the early genes of the virus (Basilico, C., Pharmac. Ther. 26, 235–272, 1984; Griffin, B. E. & Dilworth, S. M. Adv. Cancer Res. 39, 183–268, 1983; Tooze, J. DNA Tumor Viruses, Cold Spring Harbor Press, N.Y., 1981). The inoculation of rodents with killed cells transformed by PY enables an immunity to be induced against a test inoculation with tumor cells induced by PY (Sjogren et al.; Habel et al.). However, the demonstration of the presence of tumor-specific transplantation antigens and their relationship with T antigens, the synthesis of which is controlled by the early region of the PY viral genome, has not yet been clearly established. This study is complicated by the fact that the early region of the PY genome codes simultaneously for 3 separate proteins (Tooze et al.) called "large-T:LT", "middle-T:MT" and "small-T:ST", in accordance with their respective molecular weights; these 3 antigens have the same N-terminal sequence and are recognized by the same polyclonal antibodies.

As will be described in the examples, the 3 T antigens have been cloned and expressed separately, in order to define accurately their roles and their respective potentials.

The use of vaccinia virus as cloning and expression vector for foreign antigens has already been described (Panicali, D. & Paoletti, E., Proc. Natl. Acad. Sci. USA 79, 4927–4931, 1982; Mackett, M., Smith, G. L. & Moss., B., Proc. Natl. Acad. Sci. USA 79, 7415–7419, 1982). Recombinant viruses expressing antigens of heterologous viruses or of parasites have been employed to immunize animals against the corresponding pathogen (see review in Smith, G. L., Mackett, M. & Moss, B. Biotechnol. Genet. Eng. Rev. 2, 383–407, 1984). The antigens expressed by recombinant vaccinia virus are presented in the appropriate manner on the surface of infected cells and they enable a cell-type immune response to be induced (Wiktor, T. J., MacFarlan, R. I., Reagan, K. J., Dietzschold, B., Curtis, P. J., Wunner, W. H., Kieny, M. P., Lathe, R., Lecocq, J. P., Mackett, M., Moss, B. & Koprowski, H., Proc. Natl. Acad. Sci. USA 81, 7194–7198, 1984; Wiktor, T. J., Kieny, M. P. & Lathe, R., Appl. Virol. 2, in press, 1986; Bennik, J. R., Yewdell, J. W., Smith, G. L., Moller, C. & Moss, B., Nature 311, 578–579, 1984; McMichael, A. J., Michie, C. A., Gotch, F. M., Smith, G. L. & Moss, B., J. Gen. Virol. 67, 719–726, 1986), which is particularly advantageous because it is known that the removal of tumor cells involves cellular immunity (Hellstrom, K. E. & Hellstrom, I., Adv. Cancer Res. 12, 167–223, 1969; Heberman, R. B. Adv. Cancer Res. 19, 207–263, 1974).

The virus will comprise the whole range of elements required for the expression of T protein in higher cells; it will comprise, in particular, a promoter originating from the vaccinia virus. For example, the promoter of the 7.5 Kd protein gene can be employed. The promoter/T coding sequence assembly will be inserted into a non essential gene of the virus: for example, the gene for thymidine kinase (TK), which will enable the TK⁻ recombinant viruses to be selected easily.

The following examples illustrate the concept on which the invention is based, in an animal model consisting of rat tumor cells and a T antigen coded by the polyoma virus PY which is responsible for tumor production; other examples are related to the expression of early non structural genes of papillomaviruses such as BPV and HPV. However, it is obvious that similar results could be obtained with any other tumor-specific antigen which is absent or very poorly expressed in normal adult tissues or which is encoded by an oncogenic virus, and that the use of these different T antigens also forms part of the invention.

Among other T antigens which may be employed as the target in the process according to the present invention, there may be mentioned antigens specific for colorectal carcinoma, melanoma, cancer of the kidney, neuroblastoma, carcinoma of the bladder, carcinoma of the breast, lymphomas and adenomas of endocrine glands.

The tumor antigens which are used as target in the present invention may be antigens coded by viruses responsible for the transformation of cells into cancer cells, in particular viruses such as papillomas or polyomas, or, more generally, constituents of the host, the expression of which is altered in the tumor tissue.

Therefore, a further object of the invention is to produce active vaccines for preventive or curative purposes against tumors resulting from a pre-established infection by human papillomavirus (HPV).

Papillomaviruses represent a group of DNA viruses. They possess a protein shell and a circular DNA genome of approximately 7900 base pairs. A number of types of papillomaviruses, bovine (BPV) and human (HPV), have been identified, and the genomes of some of these have been fully sequenced (Pfister, H., 1987, in: The Papovaridiae: The papillomaviruses (editors, Salzman, N. P. and Howley, P. M.) Plenum Press, New York, p. 1–38).

Fundamental research work which has been carried out on these viruses has thus led to an early region and a late region being distinguished in their genome, by analogy with the polyoma and SV40 virus genome. The late region contains two reading frames L1 and L2, which code for the major components of the capsid. The early region contains at least the reading frames E1, E2, E4, E5, E6, E7 and E8. The proteins encoded by these reading frames possess different functions. Three of these proteins are involved in the processes of oncogenic transformation of infected cells. The E5 protein of BPV-1, which possesses considerable transforming power and which can transform cells in vitro independently (Schlegel, R. et al., 1986, Science 233, 464–467), is encoded by the 3' portion of the early region. The E6 protein of BPV-1 and E7 protein of HPV-16 are encoded by the 5' portion of the early region, and are involved in the induction and maintenance of oncogenic transformation. These proteins appear to be derived from a common ancestral gene by successive duplications of a peptide of 33 amino acids (Danos, O. and Yaniv, M., 1987, in: Cancer Cells, 5: Papillomaviruses, Cold Spring Harbor Laboratory, Cold Spring Harbor, N.Y.). The transforming power of E7 has been demonstred for HPV-16 and 18 (Kanda, T. et al., 1988, J. Virol., 62, 610–613; Vousden, K. H. et al., 1988, Oncogene Res., 3, 1–9; Bedell, M. A. et al., 1987, J. Virol., 61, 3635–3640). Among the other early proteins, E1 and E2 possess a role in the replication and/or expression of the virus, whereas no function has been demonstrated in E4 and E8.

In man, HPVs are associated with pathological conditions ranging from benign infection of the skin to warts and malignant tumors. These viruses are highly specific for the target tissues, in particular the epithelia of the epidermis of the genital, oral and respiratory tracts (Zur Hausen, H. and Schneider, A., 1987, in: The Papovaviridae: The papillomaviruses (editors, Salzman, N. P. and Howley, P. M.) Plenum press, New York, p. 245–263). The epidemiological data strongly suggest the role of certain strains of HPV in cancer of the neck of the uterus and of the lower passages (most frequently fatal tumor in women). HPV-16 and HPV-18 DNA are found in most biopsies originating from genital cancer cells; more rarely, HPV-31, HPV-33, HPV-35, HPV-39 and HPV-45 are detected.

Pathological conditions associated with HPV viruses give rise to a therapeutic problem on account of their persistent and recurrent nature. Many approaches have already been used in the treatment of these diseases: surgery, chemotherapy, antiviral agents and immunotherapy (Weck, P. K. and Whisnant, J. K., 1987, in: The papillomaviruses (editors, Sulzman, N. P. and Howley, P. M., Plenum Press, New York, p. 393–402).

In particular, European patent publication EP-A-0 133 123 describes a vaccination approach against an infection by papillomaviruses, which consists in preparing by genetic engineering proteins of the viral capsid, that is to say structural proteins hence corresponding to the late region of the virus, and in using them as immunogenic agents. In this document, the means described are directed towards protection against an infection by the viruses themselves, and hence theoretically against all forms of infections liable to develop.

The present invention is directed more precisely to the production of active vaccines, for preventive or curative purposes against malignant tumors resulting from a pre-established infection by HPV.

The present invention is based on the observation that the formation of tumors induced by papillomaviruses is due to the expression of the early genes of the viruses.

The subject of the invention is hence a vaccinia virus which comprises a heterologous DNA sequence coding at least for the essential region of a non structural protein of a papillomavirus, as well as the regulatory elements required for its expression in higher cells.

In view of the observations which have been made, and stated above, regarding the frequency of infection by type 16, 18, 31, 33, 35, 39 and 45 HPV in cases of cancer of the neck of the uterus, the invention aims more especially at providing vaccinal compositions which are useful against HPV-16, HPV-18, HPV-31, HPV-33, HPV-35, HPV-39 and HPV-45.

Thus, the subject of the invention is a vaccinia virus which comprises at least one DNA sequence coding for at least one non-structural protein of type 16, 18, 31, 33, 35, 39 or 45 HPV virus, and especially of the HPV-16 virus.

As stated above, the structure of the viruses of the papilloma family, especially BPV-1 and HPV, is such that there are at least 7 reading frames capable of corresponding to protein functions very specific to the mechanisms of action of the virus and of maintenance of the viral genome. Thus, it can be advantageous to prepare vaccinia viruses which express several proteins simultaneously in the human body. This may be obtained either with several vaccinia viruses each expressing a given protein, or with one vaccinia virus containing several heterologous DNA sequences corresponding to the proteins chosen.

Naturally, the recombinant vaccinia virus will contain the assembly of elements needed for expression of the proteins in higher cells, i.e. generally a transcription promoter of the gene and a region for translation initiation in the host cell; preferably, the promoter will usually be a promoter of a gene of the vaccinia virus used, such as the promoter of the gene for the 7.5K protein of vaccinia virus, as indicated above. The promoter-coding sequence assembly will be inserted into a non essential region of the virus, for example the thymidine kinase (TK) gene, thereby permitting ready selection of the TK⁻ recombinant viruses.

The present invention also relates to pharmaceutical compositions for preventing or curing tumors, containing an an active agent at least one of the recombinant vaccinia viruses of the invention.

The vaccinal compositions according to the invention may be used for a variety of purposes. They may be used preventively, to prevent the appearance of malignant tumors, either before any infection by the virus or alternatively after an infection which has caused benign disorders, so as to avoid the situation where other tissues are attacked and become transformed to cancerous tissues. They may also potentially be used curatively, to cause an already established tumor to disappear, or to complement or as a substitute for an ablation. These uses can relate to both man and animals, especially cattle for the prevention of infections by BPV viruses. The recombinant vaccinia virus may be used, where appropriate, with a pharmaceutically acceptable vehicle for its inoculation into man or animals.

In general, the live virus is inoculated into man or animals. Nevertheless, it is also possible to envisage injecting into man or animals the killed recombinant virus, presenting the chosen proteins at its surface, or the proteins purified from cell cultures infected by the recombinant vaccinia viruses.

The pharmaceutical compositions according to the invention may be prepared according to methods known in the vaccine field, and the doses applicable may vary over a wide range. They will be dependent, in particular, on the patient's state and on other parameters which will be evaluated by the practitioner.

The invention will be illustrated by the examples below, which describe results of vaccination on animals which have been injected with cells transformed by polyomavirus (PY), bovine papillomavirus (BPV-1), and by human papillomavirus (HPV-16). In particular, the cloning and sequencing of the DNAs corresponding to the reading frames for the E5, E6 and E7 proteins of HPV-16, as well as the results of vaccination obtained with recombinant viruses expressing these proteins, are described.

BRIEF DESCRIPTION OF THE DRAWINGS

The detailed description of the invention will be accompanied by FIGS. 1 to 12 which show:

FIG. 5 shows the latency period of the development of tumors in animals vaccinated with the recombinant vaccinia viruses expressing the product of the reading frames E1, E2, E5, E6 or E7 of bovine papillomavirus BPV-1 (VVbE1, VVbE2, VVbE5, VVbE6 and VVbE7), or a control recombinant vaccinia virus VV-0 (not expressing a protein of BPV-1), and tested with FR3T3 cells transformed by BPV-1 (FR3T3 BPV-1-6).

FIG. 6 shows the latency period of the development of tumors in animals vaccinated with the recombinant vaccinia viruses expressing the products of the reading frames E5, E6 and E7 of bovine papillomavirus BPV-1 (VVbE5, VVbE6, VVbE7) or a VVbE5–VVbE6 or VVbE5–VVbE7 combination, or a controlled recombinant vaccinia virus VV-0 (not expressing a protein of BPV-1), and tested with FR3T3 cells transformed by BPV-1 (FR3T3-BPV-1-3).

FIG. 9 shows the complementary DNA sequence of the reading frame E5 (HPV-16).

EXAMPLE 1

Construction of 3 recombinant vaccine viruses, each expressing one of the T antigens of the PY virus.

The coding sequences for the 3 T antigens of PY virus have already been cloned after their introns were removed by excision in vitro (1–2), to give the plasmids pPY-LT1, pPy-MT1, pPY-ST1 (2). These coding sequences were recovered by digestion with BglI at one end and HindII for LT, EcoRI for MT and PvuII for ST at the other end. The BglI end was made compatible with a BamHI site by use of a single-stranded synthetic adapter (3.):

5'-d.GATCTGG-3'

Figure 1:
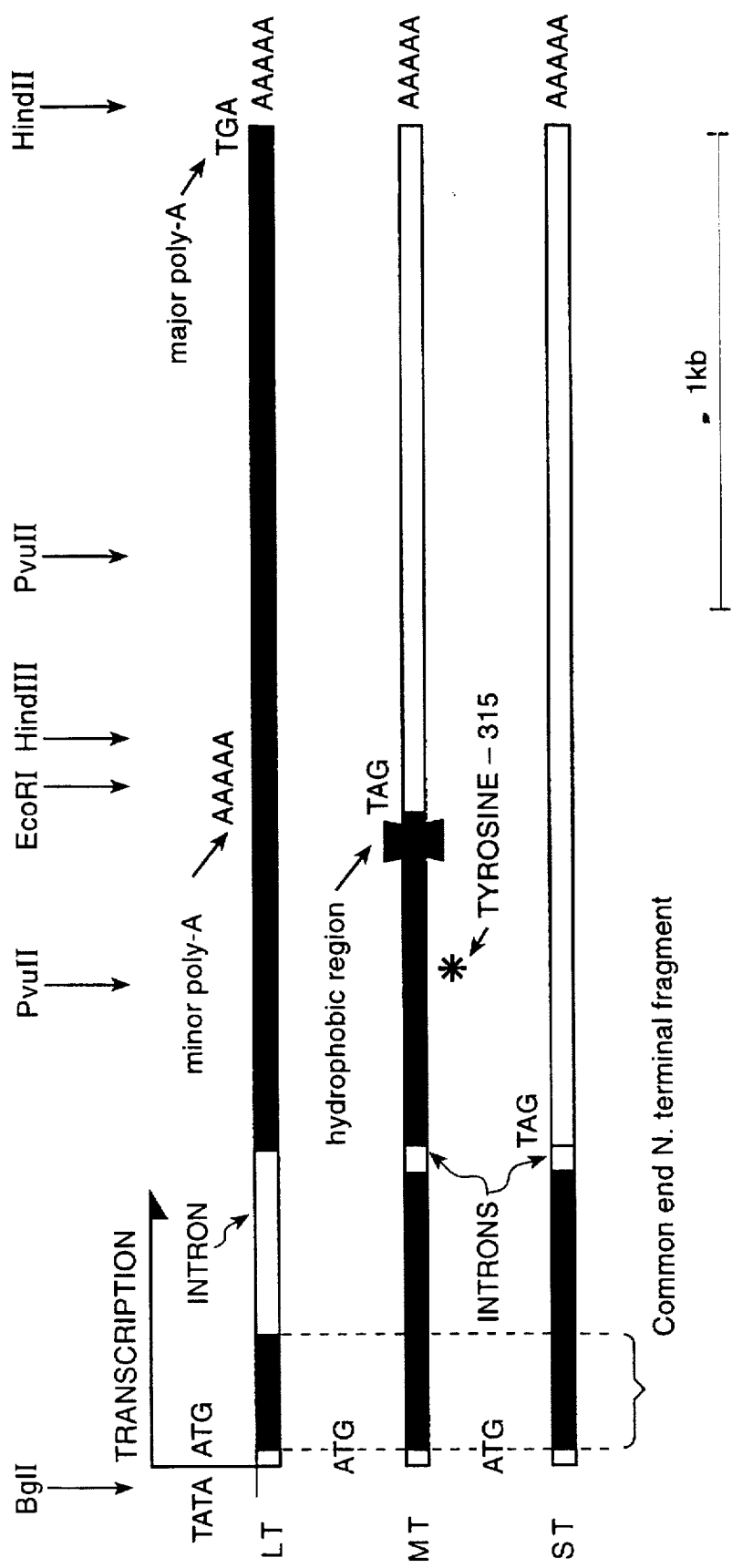
FIG. 1 shows the structure of the early region of PY DNA and demonstrates the 3 genes LT, MT and ST which overlap and, in particular, the corresponding portion of the N-terminal region which is common to them. The transcription initiation site, in PY, is indicated by TATA and the translation initiation and termination signals are denoted by ATG and TGA respectively. The position of introns as well as that of the polyadenylation sites are indicated.
Figure 2:
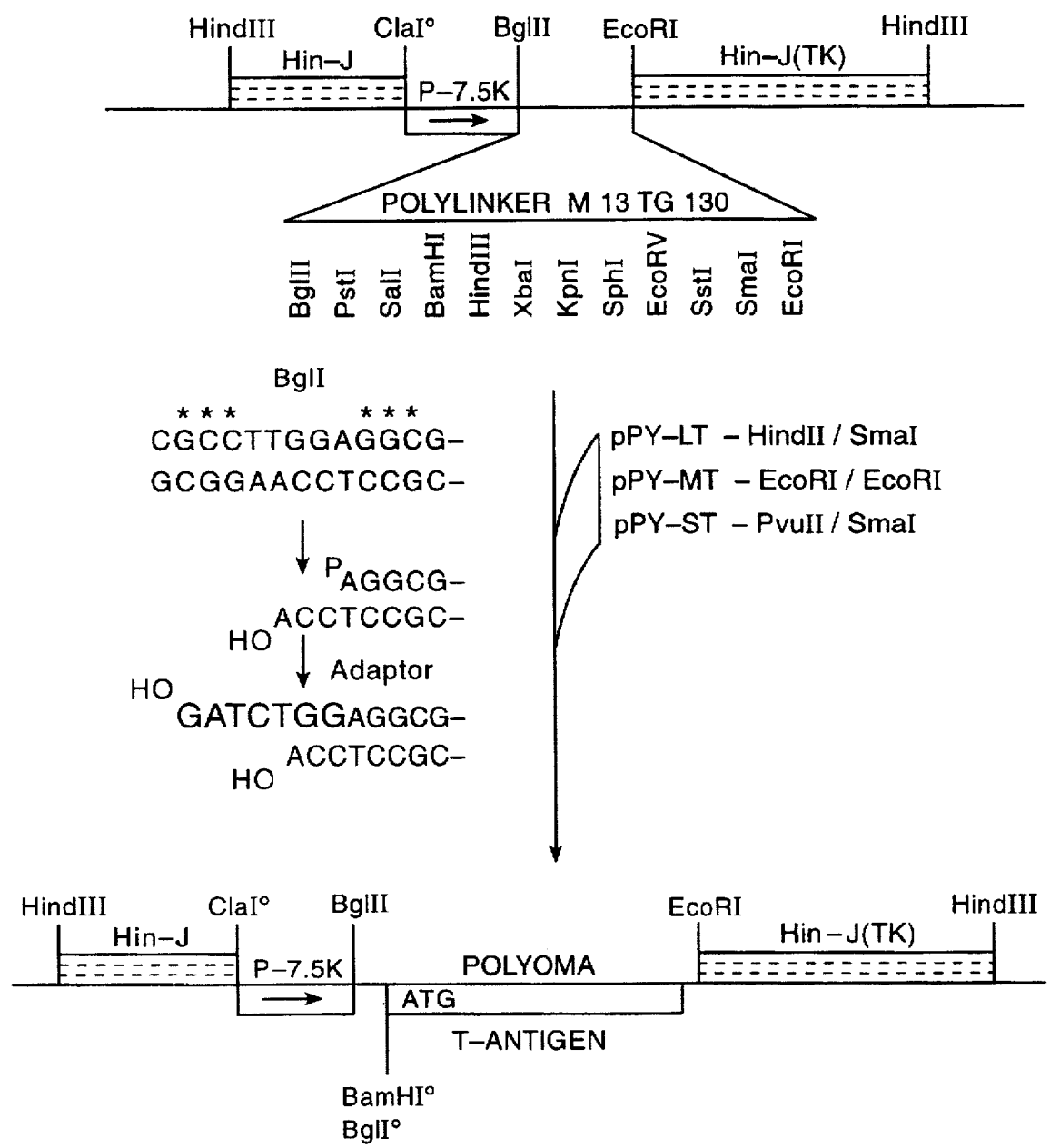
FIG. 2 shows the construction of three recombinant vaccine viruses, each expressing one of the T antigens of the PY virus.
Figure 3A:
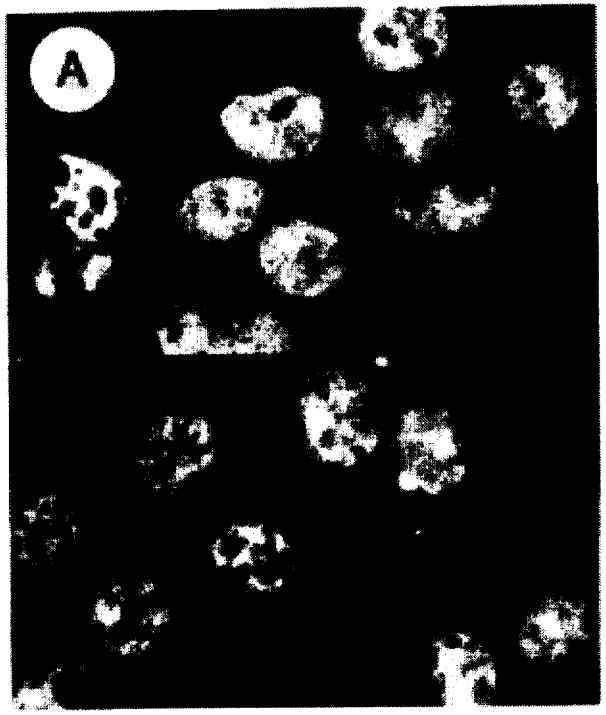
FIG. 3 shows the immunofluorescence of cells infected with VV.PY.LT (A), VV.PY.MT (B), VV.PY.ST (C) and of uninfected cells (D).
Figure 3B:
Figure 3D:
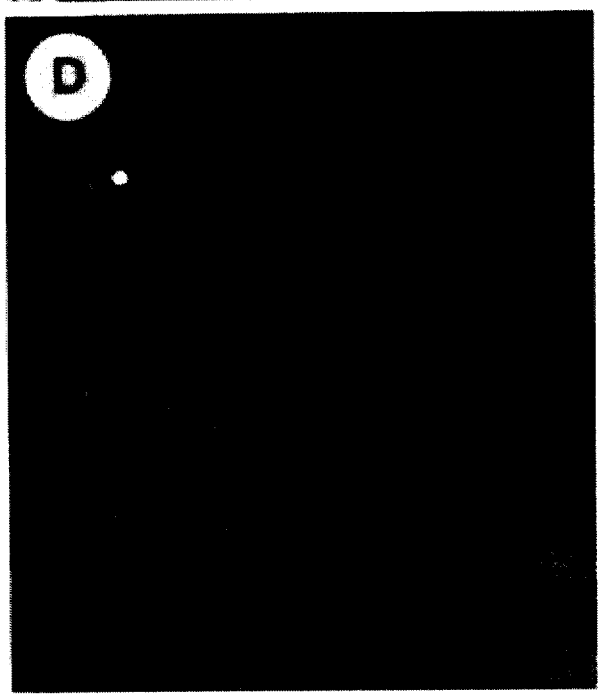
Figure 3C:

The 3 DNA segments thus treated were introduced into the pTG186-poly vector between the BamHI-SmaI, BamHI-EcoRI and BamHI-SmaI sites respectively (FIG. 2). The pTG186-poly vector results from the insertion of M13TG131 polylinker (41) which provides several restriction sites to the pTG1H-TK-7.5K vector (4) downstream of the promoter for the 7.5K gene of the vaccine virus, which itself is inserted into the TK gene of the vaccine. The 3 coding sequences for T antigens and their translation initiation and termination signals respectively have been inserted into a nonessential gene of the vaccine virus, after being placed downstream of a promoter for the vaccine virus. Following a double recombination, in cells infected with the wild virus and transfected with the recombinant plasmid, as has already been described previously (4), the coding sequence for T antigen finds itself integrated into the genome of the vaccine-virus. The recombinant viruses carrying the foreign gene are selected for their TK⁻ character by multiplication in TK⁻ 143 B cells, in the presence of 5-bromodeoxyuridine.

The recombinant viruses, having integrated the coding sequences for T antigens, have been identified by southern blotting, and 3 representative viruses were chosen: VV.PY.LT-H, VV.PY.MT-I and VV.PY.ST-J.

EXAMPLE 2

In vitro study of the properties of T antigens synthesized by VV-PY recombinant viruses.

The 3 T antigens expressed by the recombinant vaccine viruses are recognized by antibodies directed against the native PY T antigen.

The intracellular localization of antigens was studied using fluorescent antibodies: semiconfluent hamster (BHK21) cells were infected separately with the types of VV.PY.T recombinant viruses (0.1 pfu/cell; incubation overnight); the T antigens were revealed,; in cells fixed with acetone (80% concentration), by the sequential application of hyperimmune rat antiserum, anti-T (RAF no. 4, CNRS-Nice (5); 1/50 PBS+1% bovine serumalbumin), followed by fluorescent antirat antibodies (goat immunoglobulins, supplied by Miles, 1/100 PBS+1% bovine serum albumin). The 2 antibodies are each adsorbed for 20 minutes at 37° C. and the cells are then washed in order to remove the unbound antibodies. FIG. 3 shows the immunofluorescence of cells infected with VV.PY.LT (A), VV.PY.MT (B), VV.PY.ST (C) and of uninfected cells (D).

It is seen from FIG. 3 a that, as expected (6), the LT protein is located exclusively in the nucleus; the ST protein is located mainly in the cytoplasm (FIG. 3c); the MT protein is located mainly in the cytoplasm (FIG. 3b) and not on the surface, as has been reported (7). Its detection, which is weak, but reproducible, in the perinuclear region suggests an association with the Golgi apparatus and other intracellular membranes, as has been indicated by other recent studies (8,9).

EXAMPLE 3

Study of the immune response induced in animals inoculated subcutaneously with the recombinant viruses.

In order to assess the vaccination potential of the 3 VV-PY recombinants, their capacity to induce an antitumor immune response was determined in vivo.

It is known that rats inoculated subcutaneously with syngeneic cells transformed by PY quickly develop tumors located at the transplantation site. This experimental model must enable the induction of an immune response capable of blocking the development of the tumor to be demonstrated.

Groups of 4-week old female rats (Fischer) were inoculated subcutaneously with the different recombinant viruses (at a dose of $10^7$ pfu in 100 µl), reinoculated with the same dose after 12 days and then subjected to a test inoculation, on the 16th day, with 3T3 rat cells transformed by complete PY (PYT-21), at a dose of $2\times10^4$ cells in 100 µl. One group of rats was inoculated with the 3 recombinant viruses simultaneously in order to demonstrate any cumulative effect of the 3 T antigens, as has already been suggested (2).

The results are given in Table I:

All the nonvaccinated animals monitored develop tumors which can be detected within 14 days from inoculating the transformed cells; additionally, no spontaneous regression is observed during the experimental period (42 days).

The animals vaccinated with VV.PY.LT and VV.PY.MT develop small tumors (of a diameter >5 mm) which regress rapidly, to be totally eliminated in 50 to 60% of animals.

The animals vaccinated with VV.PY.ST develop tumors which do not regress with time. Therefore, the effect observed with VV.PY.LT and MT is quite specific and cannot be attributed to a nonspecific stimulation of the immune system by the vaccine virus, which is a very good immunogen and could have had a mode of action similar to that of BCG (10).

The simultaneous inoculation of the 3 recombinants does not give a significant improvement.

TABLE I

Rejection of tumors by rats inoculated subcutaneously with VV.PY.T recombinants

| Vaccine virus | Time after challenge: | Number of animals rejecting the tumor/total number inoculated | | | |
|---|---|---|---|---|---|
| | | 18 days | 21 days | 27 days | 35 days |
| | | 0/4 | 0/4 | 0/4 | 0/4 |
| VV.PY.ST | | 0/7 | 0/7 | 0/7 | 0/7 |
| VV.PY.MT | | 0/10 | 1/10 | 3/10 | 6/10 |
| VV.PY.LT | | 0/10 | 0/10 | 2/10 | 5/10 |
| VV.PY.LT +VV.PY.MT +VV.PY.ST | | 2/4 | 2/4 | 1/4 | 1/4* |

Note: *1 animal did not develop any detectable tumor until the 35th day after the challenge.

The animals were sacrificed after 42 days and their sera were analysed (Table II). All the vaccinated animals have high antibody titers against the vaccine virus and against the cells transformed by PY, irrespective of whether they were capable of rejecting tumors or not.

Therefore, it seems that the rejection of tumors cannot be attributed to circulating antibodies, but requires the participation of another immune mechanism.

TABLE II

Antibody titers in vaccinated and challenged animals, sacrificed after 42 days

| Vaccine virus | Diameter of the tumor (in mm) | Antibody titers* against | | | |
|---|---|---|---|---|---|
| | | the vaccine | (mean) | the cells transformed by PY | (mean) |
| | 15 | 1.8 | | 13.7 | |
| | 20 | 6.9 | (7.9) | 10.2 | (12.3) |
| | 15 | 15.9 | | 7.3 | |
| | 5 | 6.7 | | 18.0 | |
| VV.PY.ST | 15 | 253 | | 56.5 | |
| | 10 | 220 | (224) | 26.1 | (37.0) |
| | 15 | 218 | | 31.6 | |
| | 20 | 203 | | 33.8 | |

TABLE II-continued

Antibody titers in vaccinated and challenged animals, sacrificed after 42 days

| Vaccine virus | Diameter of the tumor (in mm) | Antibody titers* against |  | | |
|---|---|---|---|---|---|
| | | the vaccine | (mean) | the cells transformed by PY | (mean) |
| VV.PY.MT | — | 227 | | 35.9 | |
| | — | 258 | (243) | 32.6 | (30.7) |
| | — | 266 | | 28.4 | |
| | 10 | 222 | | 25.9 | |
| VV.PY.LT | — | 226 | | 11.8 | |
| | 14 | 226 | (243) | 21.2 | (37.9) |
| | — | 227 | | 30.9 | |
| | — | 295 | | 87.8 | |
| VV.PY.LT | — | 180 | | 16.0 | |
| +VV.PY.MT | 15 | 300 | (247) | 23.4 | (22.8) |
| +VV.PY.ST | 3 | 252 | | 33.9 | |
| | 8 | 255 | | 17.9 | |

*Antibodies were determined on microtiter plates with purified vaccine virus ($10^6$ pfu in 100 µl) or PYT-21 cell suspension ($10^5$ cells in 100 µl); bound antibody is detected by the sequential addition of sheep antirat IgG, labelled with biotin (Amersham) and then streptavidine peroxidase (Amersham) followed by the ragent ELAVIA-R9 (Pasteur-Diagnostic). The absorption at 492 nm is measured with a Titertec-uniscan plate reader. Antibody titer is given by the product of multiplication of the measured optical density by the dilution of the anti-serum employed. Each result is the mean value of 3 dilutions (1/50, 1/250 and 1/1,250).

EXAMPLE 4

Rejection of tumors in animals vaccinated intradermally with the recombinant viruses.

Another route for inoculating the vaccine virus was tried.

Groups of 4-week old female rats (Fischer) were vaccinated intradermally, by scarifying the base of the tail with a scalpel, with purified virus (10 µl of a $2 \times 10^9$ pfu/ml stock).

A second dose is inoculated after 15 days. The animals are subjected to test inoculation, by injecting $2 \times 10^4$ PYT-21 cells in 100 µl subcutaneously, 4 days later.

The results are given in Table III.

TABLE III

Rejection of tumors by rats inoculated intradermally with the VV.PY.T recombinants

| Vaccine virus | Time after challenge: | Number of animals rejecting the tumor/total number inoculated | | |
|---|---|---|---|---|
| | | 22 days | 29 days | 39 days |
| | | 0/4 | 0/4 | 0/4 |
| VV.PY.ST | | 0/4 | 0/4 | 0/4 |
| VV.PY.MT | | 2/8 | 7/8 | 8/8 |
| VV.PY.LT | | 0/8 | 0/8 | 5/8 |

EXAMPLE 5

Treatment of tumor bearing animals with the VV.PY.T. recombinant viruses.

Recombinant virus administration was attempted as curative treatment for tumors.

10 rats which were inoculated with cells transformed by PY and which had developed a tumor were inoculated with the VV.PY.LT recombinant after 12 to 16 days; the tumor was 2 to 3 mm in size at the time of the first inoculation.

In all the animals, the tumor continued to grow until it reached a diameter of 15 mm. In 2 animals, the tumor then regressed significantly (observation made on the 35th day) and was then completely eliminated.

No similar result was observed either with VV.PY.MT or with VV.PY.ST, which indicates differences in immunogenicity between the 3 types of T antigen.

Deposition of a representative strain of the invention

The vector plasmid in which any coding sequence for a T antigen may be integrated so as to be later recombined in the vaccine virus was deposited at the Collection Nationale de Cultures des Microorganismes (National Collection of Microbial Cultures) under the no. I 458, on Jun. 20, 1985.

This *E. coli* plasmid derived from pML2 comprises a replication origin in *E. coli*, the β-lactamase gene, the vaccine TK gene, interrupted by the 7.5K promoter of the vaccine and a following coding sequence (human IL2 sequence), which can be exchanged with the sequence coding for a T antigen.

EXAMPLE 6

Inhibition of the development of tumors induced by bovine papillomavirus (BPV-1), by vaccination with recombinant vaccinia viruses expressing the early proteins of BPV-1.

a) Construction of vaccinia viruses expressing the early proteins of BPV-1

Plasmid pm69 (11) contains the early region of the BPV-1 genome inserted as a HindIII-BamHI fragment into the HindIII and BamHI sites of plasmid pML2 (11). Subfragments containing the reading frames E1, E2, E5, E6 and E7 are excised by digestion with restriction enzymes (see Table I) and introduced into the bacteriophages M13TG130 or M13TG131 (12) and then subjected to an oligonucleotide-directed localized mutagenesis before being transferred into plasmid pTG186 poly (13). These steps are summarized in Table IV.

Legend to Table IV:

[a]: the underlined nucleotides specify the bases not matched to the parent sequence of BPV-1

[b]: the translation initiation codon and the restriction site which are used in the cloning are underlined.

[c]: it was not possible to introduce the EcoRI-BamHI fragment of plasmid pM69 containing the reading frame E5into the bacteriophage M13TG131 in the desired orientation: clones are obtained in the reverse orientation in which two independent plasmid fragments are cloned; the oligonucleotide-directed mutagenesis hence corresponds to the other strand of the DNA.

[k]: end produced by digestion with a restriction enzyme followed by treatment with the Klenow fragment of *E. coli* DNA polymerase I before cloning;

na: not applicable.

TABLE I

Cloning and mutagenesis of subfragments of the BPV-1 genome for their transfer into vaccinia viruses.

| BPV-1<br>• reading frame<br>• fragment | • vector<br>• site | Mutagenesis<br>• sequence (5'-3')<br>of oligonucleo-<br>tides used [a]<br>• sequences at the<br>translation inititiaton site [b] | Cloning<br>• fragment<br>• vector<br>• site |
|---|---|---|---|
| E1<br>NruI-AvrII | M13TG130<br>BamHI]k]-XbaI | na<br>(TCGCGAGCGTCATGG) | BamHI-SstI<br>pTG186poly<br>BamHI-SstI |
| E2<br>EcoRI-SpeI | M13TG131<br>EcoRI-XbaI | GAGGAGGATCCTGAAGAGGA<br>(GGATCCTGAAGAGGATGG) | BamHI<br>pTG186poly<br>BamHI |
| E5<br>EcoRI-BamHI | M13TG131<br>EcoRI-BamHI | AGATTTGCCATAGTCGACCAGTCA[c]<br>(GTCGACTATGG) | SalI-BamHI<br>pTG186poly<br>SalI-BamHI |
| E6<br>HpaI-SmaI | M13TG130<br>SmaI | CAGACCCCGGATCCAACATGGACCT<br>(GGATCCAACATGG) | BamHI-XmaIII[k]<br>pTG186poly<br>BamHI-SmaI |
| E7<br>HpaI-SmaI | M13TG130<br>SmaI | TGCTAGGACTCGAGCAAACATGGTTCA<br>(CTCGAGCAAACATGG) | XhoI-EcoRI<br>pTG186poly,<br>SalI-EcoRI |

Oligonucleotide-directed localized mutagenesis permits the introduction of a translation initiation consensus sequence at the initiation codon so as to provide for the correct expression after transfer into vaccinia virus. In each case, the synthetic oligonucleotide introduces a single restriction site immediately before the sequence determining the beginning of translation.

In the case of the reading frame of E1, it is not necessary to carry out a localized mutagenesis due to the presence of a restriction site in the BPV-1 genome (NruI site in position −11 relative to the initiation ATG (lacuna) and of a quasi-consensus sequence of the translation initiation region (GCGTCATGG): the nucleotide G in position −3 is almost as effective as A in translation initiation.

Primary chick embryo cells are cultured at 37° C. in an MEM medium (Gibco) supplemented with 10% of fetal calf serum. They are subjected simultaneously to an infection with a temperature-sensitive vaccinia virus and to a transfection with expression/transfer vectors carrying the inserted segments of BPV-1 and wild-type vaccinia virus DNA. After selection, vaccinia recombinants in which the expression of the inserted sequence is under the control of the 7.5K promoter of vaccinia virus are isolated according to standard techniques.

The recombinant vaccinia viruses (VV) expressing the early proteins of BPV-1 E1, E2, E5, E6 and E7 are referred to as VVbE1, VVbE2, VVbE5, VVbE6 and VVbE7 respectively.

b) Expression of E1, E2, E5, E6 and E7 in cells infected with the recombinant viruses BHK-21 cells on Dulbecco's modified Eagle's medium MEM.BME (GIBCO) supplemented with 10% of fetal calf serum (GIBCO) are infected with one of the six recombinant viruses at a multiplicity of approximately 20 plaque forming units (pfu) per cell.

After one hour at 37° C., fresh medium is added and the cells are incubated for two hours. The medium is withdrawn and the cells are washed once. MEM.BME medium without methionine and/or cysteine and supplemented with 5% of dialyzed fetal calf serum is then added. Labeling is performed with 0.5–1 mCi/ml of [$^{35}$S]-L-methionine and/or [$^{35}$S]-L-cysteine (Amersham) for 3 hours at 37° C. The cells thus labeled are rinsed twice with 20 mM Tris.HCl pH 7.2, 150 mM NaCl (TS buffer) containing aprotinin (1 IU/ml; Biosys, France), collected by scraping and rinsed by two centrifugations in STE buffer (20 mM Tris.HCl pH 7.2, 150 mM NaCl, 1 mM Na$_2$EDTA, 1% aprotinin). The cells are lysed in RIPA buffer [50 mM Tris.HCl, pH 7.4, 150 mM NaCl, 1 mM Na$_2$EDTA (sic), 1% Triton X-100, 1% Na deoxycholate, 0.1% SDS] or fractionated to determine the subcellular localization of the proteins of BPV-1.

Immunoprecipitation and SDS-PAGE are performed according to the procedure described by Davis (14). Rabbit polyclonal antisera raised against the bacterial fusion proteins corresponding to the reading frames E1, E2, E5, E6 and E7 are obtained by the conventional method known to those skilled in the art; see, for example, references (15) and (16).

Figure 4:
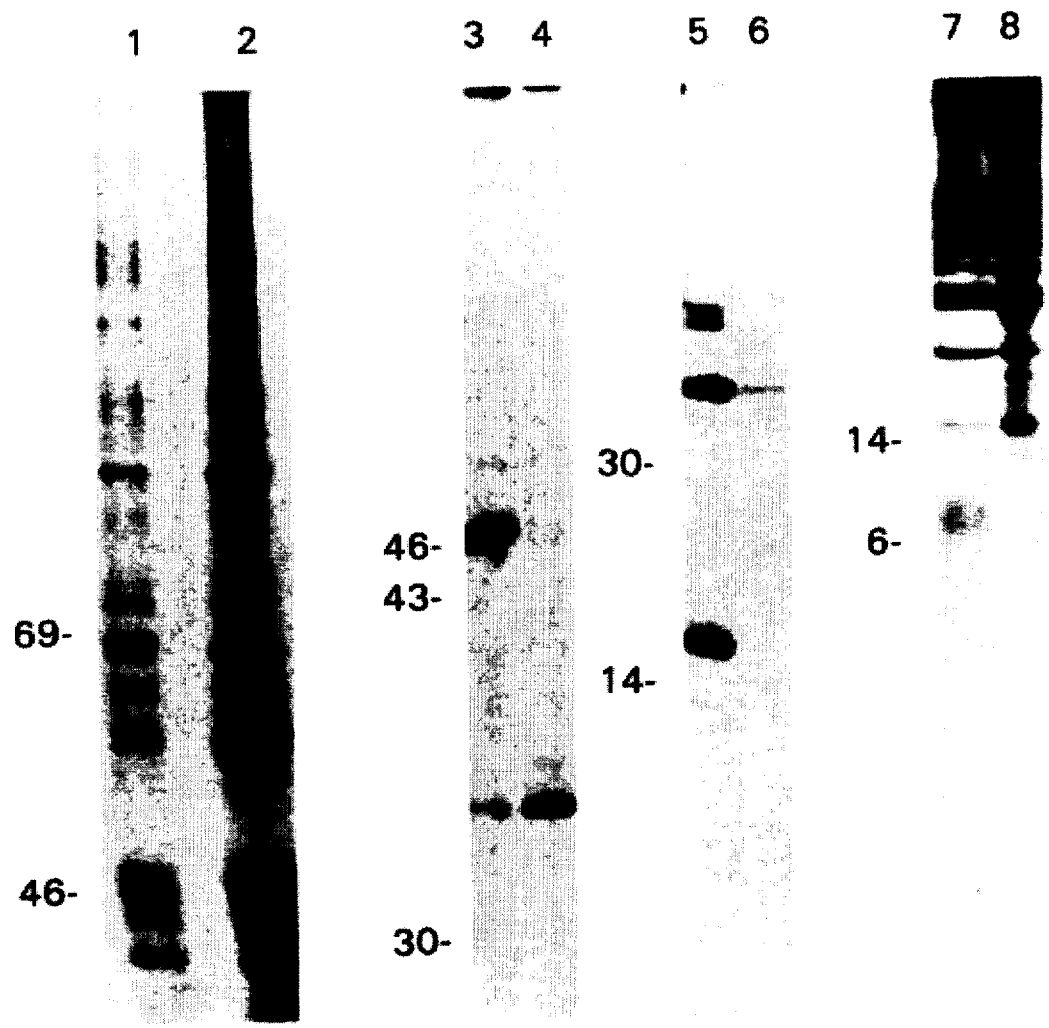
FIG. 4 shows the SDS-PAGE gel of the immunoprecipitates of the products of the reading frames E1, E2, E5 and E6 of the early region of the bovine papillomavirus BPV-1 genome.

Cells infected with VVbE1 produce a 69-kD nuclear protein which is specifically recognized by anti-E1 antiserum (FIG. 4, strip 1, strip 2 corresponds to an immunoprecipitation with a non-immune serum). Cells infected with VVbE2 contain a high level of a 48-kD polypeptide displaying a cross-reactivity with E2 and corresponding to the major transactivation protein encoded by the reading frame E2 of BPV-1 (FIG. 4, strip 3 and control strip 4). This polypeptide is detected in all the cell subfractions examined, in agreement with what has been described for the E2 protein of cells transformed by BPV-1 (17). VVbE6 codes for a 15.5-kD protein specifically precipitated by anti-E6 serum (FIG. 4, strip 6 and control strip 7) and localized to the extent of more than 50% in the cytoplasmic fraction, as for the E6 protein of cells transformed by BPV-1 (18). Cells infected with VVbE5produce a 7.5-kD polypeptide associated with the cell membranes (FIG. 4, strip 7 and control, strip 8), a localization characteristic of the E5protein of BPV-1 (19). Immunoprecipitation experiments with anti-E7 antiserum display no cross-reactivity. Nevertheless, analysis of the expression vectors reveals the presence of the reading frame of E7 in a correct orientation, and we assume that E7 is indeed produced but that, for some unknown reason, it is not precipitated by the antiserum available.

c) Vaccination against tumor cells induced by BPV-1

Groups of 4-week-old female rats (Fischer) are inoculated intradermally or intraperitoneally with the different recombinant viruses (at a dose of 10$^8$ pfu in 100 μl). They undergo a booster injection with the same dose after 12 days, and are subjected to a challenge inoculation between days 16 and 17 with Fischer rat 3T3 syngenic line (FR3T3) cells transformed by BPV-1 according to the protocol described in references (11, 20) and referred to as FR3T3-BPV-1-6. For this purpose, $2 \times 10^4$ cells are injected subcutaneously in a volume of 200 µl of MEM.BME medium without serum.

The results are shown in FIG. 5:

- all the animals monitored vaccinated with VV-0 develop tumors after a latency period of 43 days on average.
- the animals vaccinated with VVbE1 or VVbE2 show no modification in the development of tumors.
- the animals vaccinated with VVbE5, VVbE6 and VVbE7 show a significant delay in the appearance of tumors. In addition, in a few cases, there is no development of tumors (>250 days after the challenge), points shown in the box at the top of the figure.

These experiments are repeated, performing the challenge inoculation with FR3T3 line cells transformed by BPV-1 according to the protocol described in references (11, 20) and referred to as FR3T3-BPV-1-3. Since VVbE1 and VVbE2 are without effect, only VVbE5, E6 and E7 are tested, and two groups of rats are inoculated with 2 recombinant viruses simultaneously, either VVbE5 and VVbE7, or VVbE5 and VVbE6, in order to detect a possible cumulative effect of these antigens. FIG. 6 confirms the beneficial effect of a vaccination with VVbE5 and VVbE7 (points in the box at the top of the figure correspond to the animals which do not develop a tumor), whereas VVbE6 remains without a significant effect in this situation. In addition, no pronounced cumulative effect is seen with the VVbE5, VVbE7 combination.

EXAMPLE 7

Cloning of the HPV-16 virus genome.

CaSki line cells (ATCC 1550) contain the HPV-16 virus genome integrated in a chromosome. From 10 75-cm$^3$ flasks of semi-confluent CaSki cells, the total genomic DNA is purified in the following manner: the cells are recovered by scraping, centrifuged and washed, and then taken up in 15 ml of TE buffer [10 mM Tris pH 7.5, 1 mM EDTA] +0.5% SDS. After treatment with proteinase K (7.5 mg/15 ml) at 37° C. for 16 hours, the DNA is stored at 4° C. In this manner, 1 ml of solution containing 0.6 mg of DNA is obtained.

70 µg of this DNA are subjected to a partial digestion with the enzyme MboI (10 min; 40 units) and then deposited on a linear sucrose gradient (20%–40%). After centrifugation (rotor SW28, 16 hours at 25.000 rpm, 20° C.), 500-µl fractions are collected. The fractions containing DNA of size between 10 and 20 kb (fraction 23–26) are combined, dialyzed against TE buffer and then precipitated with ethanol. In this manner, 5 µg of DNA are obtained.

In order to have a cloning vector for the DNA described above, bacteriophage lambda EMBL 301 DNA (21) is digested with the restriction enzyme BamHI. After phenol/chloroform extraction and ethanol precipitation, the DNA is resuspended in TE buffer.

The CaSki cell genomic DNA and bacteriophage lambda DNA are then ligated according to a conventional protocol (1 µg of vector, 2 µg of genomic DNA). After packaging of the DNA by means of a kit marketed by Amersham, a total of $0.75 \times 10^6$ independent clones is obtained. These bacteriophages are plated with E. coli Q358 bacteria on 18 dishes 14 cm in diameter and on LBM medium in order to be screened with synthetic oligonucleotides deduced from the HVP-16 virus sequence [(EMBL) PA16].

The screening of the recombinant bacteriophage DNA is performed in a conventional manner for those skilled in the art. The oligonucleotides 1817 (sequence 5' CATGCATG-GAGATACACCTACATTG 3'; reading frame E7 (lacuna) and 1818 (sequence 5' GTGGATAACAGCAGCCTCT-GCGTTT 3'; reading frame E5), radioactively labeled with $^{32}$P, are mixed and hybridized with the phage DNA (transferred onto nitrocellulose filters) for 16 hours at 55° C. in a 6-fold concentrated SSC buffer. The filters are then washed under the same stringency conditions; 10 positive signals (1–10) were obtained. The area of the Petri dishes corresponding to these signals is taken up in 1 ml of LBM buffer. These suspensions are replated on Petri dishes 10 cm in diameter (2–10 µl of suspension per dish) in duplicate and a secondary screening is performed with the oligonucleotides 1817 and 1818 separately. Since the signals corresponding to the phages obtained from the first isolations 4 and 5 are the most intense, these two clones are chosen for the subsequent experiments.

Minicultures of E. coli Q358 bacteria, infected with the bacteriophage isolated from the subclones 4-1, 4-2, 5-1 and 5-2, are prepared. The DNA of these clones is purified and subjected to digestion with the restriction enzyme PstI in order to analyze the recombinants selected.

After migration on a 1% agarose gel, the above DNAs are transferred onto a nitrocellulose membrane according to Southern's technique. These membranes are then incubated with the two oligonucleotides 1817 and 1818 labeled with $^{32}$P by the action of polynucleotide kinase, as above. After hybridization and washing of the membrane, the latter is subjected to autoradiography. Two bands corresponding to DNAs of sizes 1063 and 1772 bp, respectively, are thereby visualized, indicating that the clones 4-1, 4-2, 5-1 and 5-2 possess the HPV-16 virus genome.

EXAMPLE 8

Sequencing of the DNAs corresponding to E6, E7 and E5

The bacteriophage 5-1 is chosen for the subsequent experiments. In order to have large amounts of the DNA of this clone, a DNA preparation from 500 ml of infected E. coli Q358 bacteria is made according to a conventional protocol. 800 µg of DNA are thereby obtained. After digestion with the enzyme PstI, the DNA is subjected to electrophoresis on 1% agarose gel containing ethidium bromide and visualized with a UV lamp. The gel bands corresponding to the sizes 1063 and 1772 bp are cut out and the DNA is extracted using a "Geneclean" kit (Bio101 Inc). This DNA is then ligated in a bacteriophage M13TG130 opened at the PstI site, and transformed into competent E. coli NM522 bacteria.

The recombinant bacteriophage M13 DNA is purified from minicultures (1.5 ml) and analyzed by digestion with restriction enzymes. A clone containing the 1063 bp HPV-16 band (M13 E5) and a clone containing the 1772 bp HPV-16 band (M13 E7/E6) are selected.

In order to limit the work of sequencing, and since the desired DNAs are those corresponding to the reading frames E5, E6 and E7, only the regions of the PstI restriction fragments corresponding to the E6 and E7 proteins (M13 E7/E6) and E5protein (M13 E5) are sequenced, by means of synthetic oligonucleotides of sequence 5' ATCTAACATATATTC 3' and 5' GTTGTTCCATA-CAAA 3' for M13 E7/E6 and

5' GTCTGCCTATTAATAC 3' for M13 E5.

Figure 7:
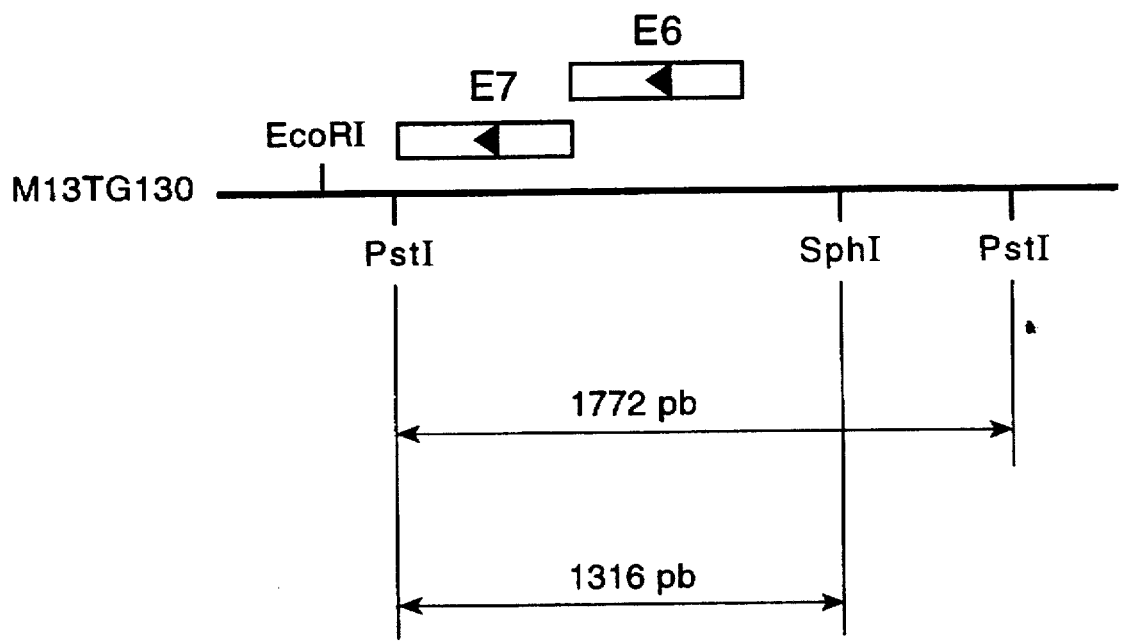
FIG. 7 shows diagrammatically the structure of the bacteriophage M13 E7/E6 (HPV-16).
Figure 8:
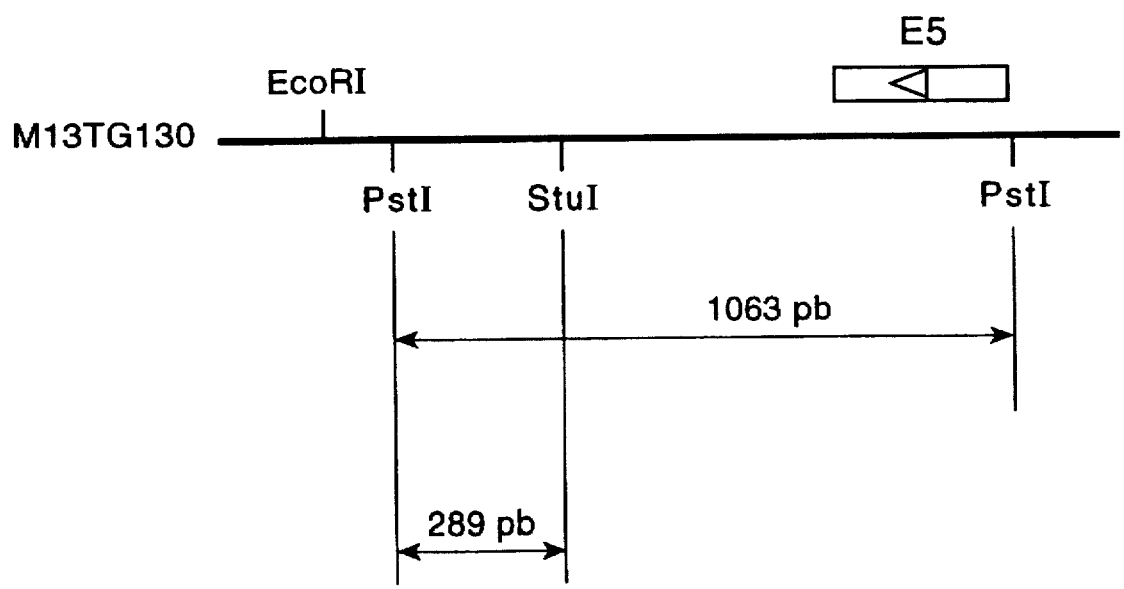
FIG. 8 shows diagrammatically the structure of the bacteriophage M13 E5 (HPV-16).

FIG. 7 shows the structure of the bacteriophage M13 E7/E6 and FIG. 5 that of the bacteriophage M13 E5. The sequence obtained for E7 reveals a total homology with the sequence contained in the libraries of PPH16 data. For E6, two mutations are observed: G in place of A in position +46 and G in place of T in position +264, relative to the initiation ATG of E6. For E5, the sequence shown in FIG. 9, which differs by a few bases from the sequence contained in the library of data, is obtained.

EXAMPLE 9

Cloning of the DNA fragments carrying E6, E7 and E5into the transfer vector.

Before integrating the DNAs coding for these 3 reading frames in recombinant vaccinia viruses, it is necessary to modify them in order to have single restriction sites upstream and downstream from the genes, and to improve the sequences around the initiation ATG in order to obtain a good translation and a high level of synthesized protein.

a) Reading frame E6

A SalI restriction site and a SphI restriction site are created upstream and downstream, respectively, from the coding sequence for E6 by means of two synthetic oligonucleotides, employing a technique of oligonucleotide-directed localized mutagenesis (Amersham kit). These two point mutations are produced simultaneously using the following oligonucleotides:

5' GTTAGTATAAAAGTCGACCCACCATG-CACCAAAAGAG 3'

5' CATGCATGCAGATACACC 3'

A nucleotide A in position −3 relative to the ATG is introduced in place of a nucleotide T at the same time as the SalI site.

The bacteriophages obtained are analyzed by digestion with restriction enzymes and by sequencing. A clone is selected for the subsequent experiments, designated M13TG1181. The SalI-SphI restriction fragment is then cloned into the vector pTG186 poly (13) opened at the SalI and SphI sites (pTG2198). This vector enables the DNA to be transferred into the vaccinia virus genome.

b) Reading frame E7

A PstI restriction site and a nucleotide A in position −3 are introduced upstream from the sequence coding for the E7 protein by localized mutagenesis by means of the following oligonucleotide:

5' GTAGAGAAACCCTGCAGCCACCATGCATGGAG 3'

Several clones were obtained. One of them, which contains a 350-bp PstI restriction fragment, is sequenced in the region corresponding to the mutation. The sequence indeed corresponds to the expected mutation (M13TG1182). The PstI restriction fragment is then inserted into plasmid pTG186 poly open at the PstI site (pTG2199).

c) Reading frame E5

A PstI restriction site is introduced upstream from the initiation ATG of the reading frame E5(position 3851 in PPH16) by localized mutagenesis by means of the following oligonucleotide:

5' GTCTACTGGATTTACTGCAGTATGA-CAAATCTTGAT 3'

An EcoRI restriction site is introduced downstream from the stop codon by means of the following oligonucleotide:

5' GTATATGTACATAATGAATTCTTA-CATATAATTGTTG 3'

These two mutations are introduced simultaneously (Amersham kit). The clone selected for the subsequent experiments is designated M13TG 3151. The PstI-EcoRI restriction fragment is then inserted into plasmid pTG186 poly opened at the PstI and EcoRI sites (pTG3180).

EXAMPLE 10

Construction of the recombinant vaccinia viruses.

Plasmids pTG2198, 2199 and 3180 are used for transferring the reading frames E6, E7 and E5into a vaccinia virus (Copenhagen strain) as described above. The recombinant viruses in which the coding sequences are under the control of the 7.5K promoter of vaccinia are referred to as VVhE6, VVhE7 and VVhE5.

BHK-21 cells on MEM.BME medium supplemented with 10% of fetal calf serum are infected with one of the three recombinant viruses at a multiplicity of approximately 20 pfu per cell.

After incubation according to the protocol described above, the cells are recovered, lysed and fractionated in order to determine the subcellular localization of the proteins of HPV-16.

The expression of the E6 and E7 genes is verified by immunoprecipitation of the proteins (labeled with [$^{35}$S]cysteine) synthesized.

Polyclonal antibodies raised against the bacterial fusion proteins corresponding to the reading frames of E6 and E7 are obtained by the conventional method known to those skilled in the art and described in references (22) and (23).

Figure 10:
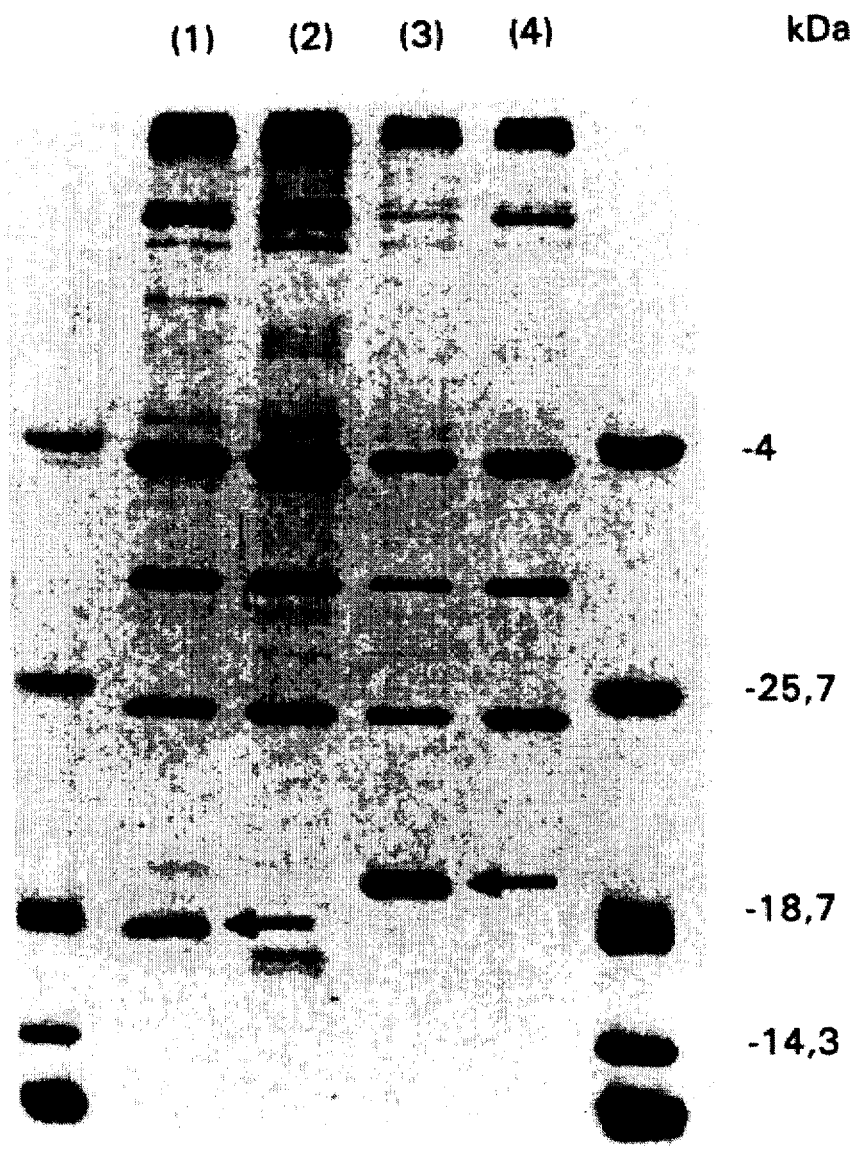
FIG. 10 shows the SDS-PAGE gel of the immunoprecipitates of the products of the reading frames E6 and E7 of the early region of the human papillomavirus HPV-16 genome.

Cells infected with VVhE6 produce an 18-kD cytoplasmic protein which is specifically recognized by anti-E6 antiserum (FIG. 10, strip 1, strip 2 corresponds to an immunoprecipitation with a non-immune serum). Cells infected with VVhE7 also produce a 19–20-kDa cytoplasmic protein specifically recognized by anti-E7 antiserum (FIG. 10, strip 3, strip 4 corresponds to an immunoprecipitation with a non-immune serum).

For E5, since no antiserum is available, the integration of the expression block E5 into the vaccinia virus is verified by DNA analysis according to Southern's technique.

EXAMPLE 11

Effect of vaccination with VVhE6 and VVhE7 on the development of tumors induced by HPV-16.

Groups of 4-week-old female rats (Fischer) are vaccinated by intradermal injection of 5×10$^7$ pfu (in 100 µl) of the different recombinant viruses. They are subjected to a booster injection with the same dose after 12 days.

Between days 16 and 17, they are challenged with a line obtained by cotransfection in primary rat cells: (RE01 line). 1) by a plasmid containing the HPV-16 genome under the control of the LTR of Moloney's retrovirus (24); 2) by a plasmid coding for a gene for resistance to G418 and for EJ-RAS, which transforms only established cell lines or lines expressing an immortalizing gene.

2×10$^4$ cells are injected subcutaneously in a volume of 200 µl of MEM.BME buffer without serum.

Figure 11:
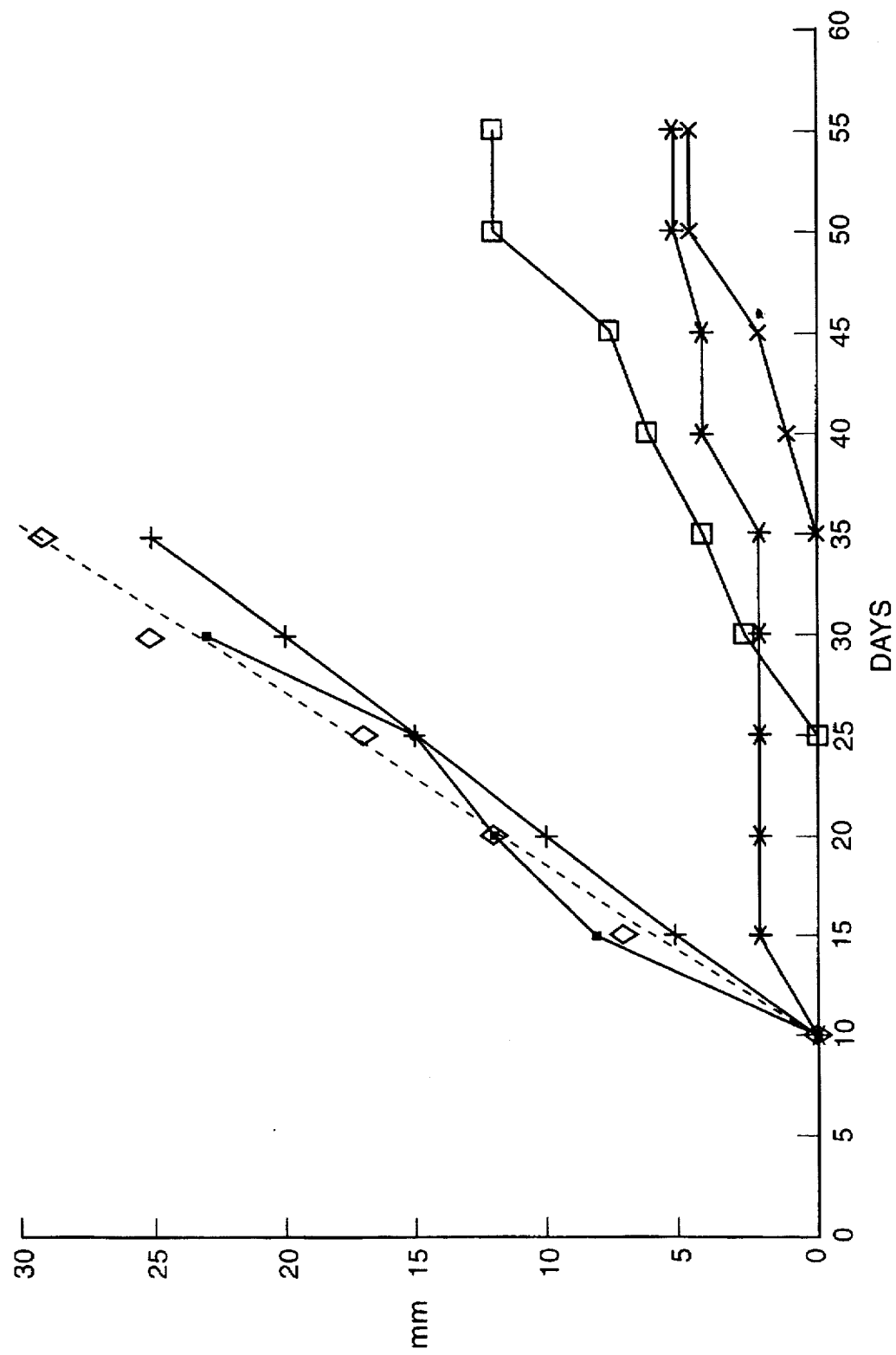
FIG. 11 shows the changes in size of the tumors in animals vaccinated with the recombinant vaccinia virus expressing the product of the reading frame E6 of human papillomavirus HPV-16 (VVhE6) and tested with primary rat cells transformed by HPV-16 and a ras oncogene.
Figure 12:
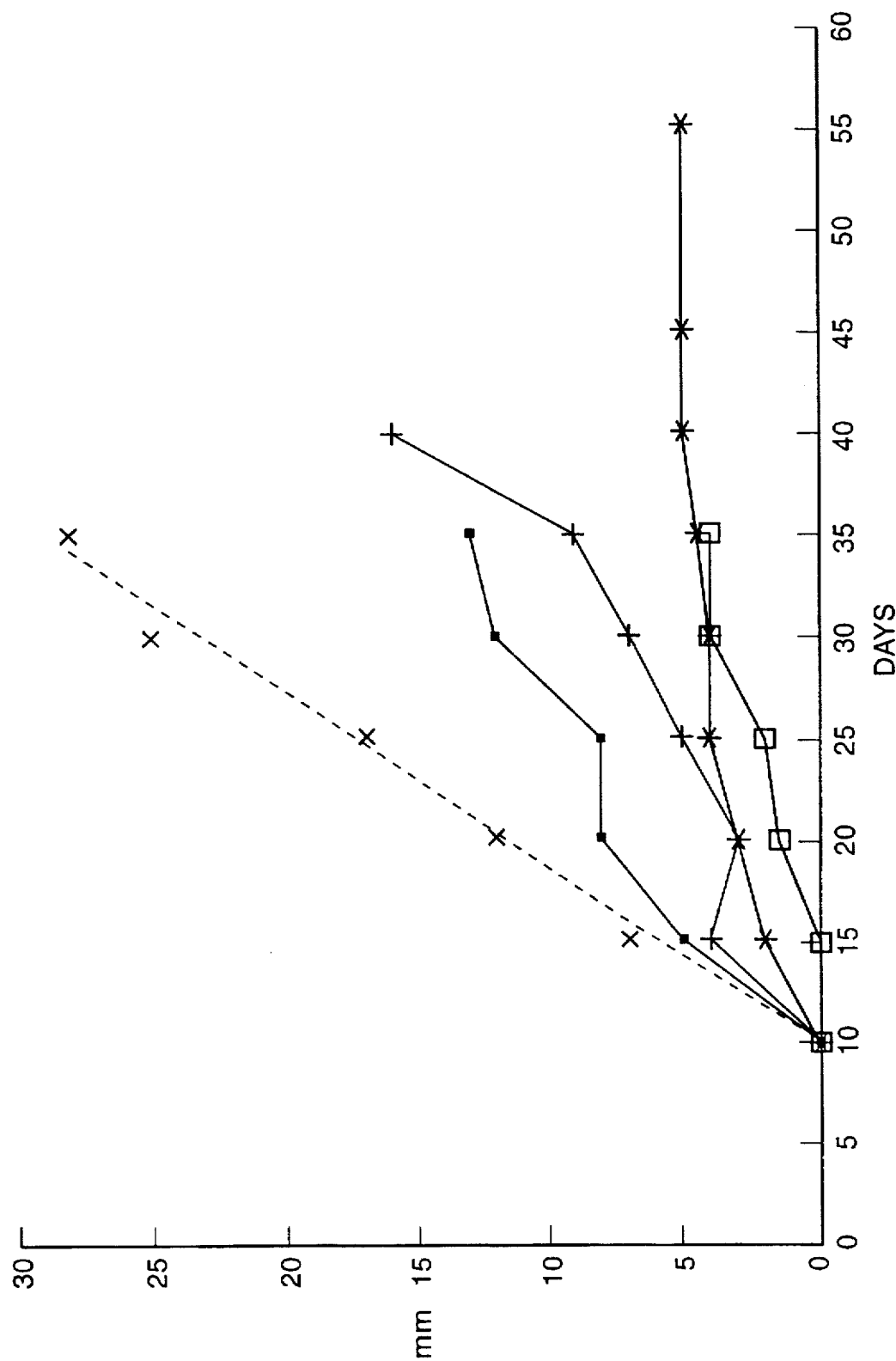
FIG. 12 shows the changes in size of the tumors in animals vaccinated with the recombinant vaccinia virus expressing the product of the reading frame E7 of human papillomavirus HPV-16 (VVhE7) and tested with primary rat cells transformed by HPV-16 and a ras oncogene.

From FIGS. 11 and 12, the following observations can be made:

- the unvaccinated control animals develop tumors detectable 10 days after the inoculation of the transformed cells (see dashed lines).
- the animals vaccinated with VVhE6 do not develop a tumor in 2 cases out of 7 (>100 days). When tumors appear, in 3 cases their development is slowed down very significantly, and for 2 animals the appearance of the tumors is delayed (24 and 34 days instead of 10 days). Finally, in two cases, the development of the tumors is identical to that shown by the animals in the control batch.

the animals vaccinated with VVhE7 do not develop a tumor in 3 cases out of 7 (>100 days). In the other 4 cases, the tumors appear from day 10 onwards, but their development is significantly retarded.

In order to test the protective effects of these vaccinations, the animals which, in the two batches, did not develop tumors are taken again and challenged 80 days after the first inoculation challenge with 10 times the initial dose, that is to say $2 \times 10^5$ cells. Under such conditions of inoculation, control animals develop tumors after 4 days.

the animals which had been vaccinated with VVhE6 develop tumors in an identical manner to the control animals.

in contrast, the animals previously vaccinated with VVhE7 do not develop tumors (>100 days) even under these conditions.

These results, as well as those stated above, bring out the important part played by the E7 antigens in protection against the development of tumors induced by HPV-16.

In order to verify the above results, two other series of experiments are carried out with other cell lines. Groups of 4-week-old female rats are vaccinated by intradermal injection of the recombinant viruses, as described above. The rats vaccinated with the recombinant viruses are challenged with $2 \times 10^4$ or $10^5$ primary rat cells (RE31 line) prepared according to the protocol described above. The number of animals which rejected the tumors, or in which a delay is observed in the appearance of the latter, is given in the first part of Table V (First challenge). In this table, VV0 corresponds to a control recombinant vaccinia virus not expressing a protein of HPV). Thereafter, rats which have rejected the tumors a first time are again challenged, but using a higher concentration of primary cells ($2 \times 10^5$ instead of $2 \times 10^4$ or $10^5$). The results obtained are presented in the second part of Table V (Second challenge).

TABLE V

| Recombinant virus | Rejection | Delay in the appearance of the tumor | Total |
|---|---|---|---|
| First challenge by injection of $2 \times 10^4$ RE31 line cells per rat ||||
| VVhE6 | 3/18 | 5/18 | 8/18 |
| VVhE7 | 3/17 | 5/17 | 9/17 |
| VV0 | 0/17 | 0/17 | 0/17 |
| First challenge by injection of $10^5$ RE31 line cells per rat ||||
| VVhE6 | 7/20 | 1/20 | 8/20 |
| VVhE7 | 5/20 | 0/20 | 5/20 |
| VV0 | 1/20 | 0/20 | 1/20 |
| Second challenge by injection of $2 \times 10^5$ RE31 line cells per rat ||||
| VVhE6 | 2/4 | 0/4 | 2/4 |
| VVhE7 | 3/4 | 1/4 | 4/4 |
| VV0 | 0/5 | 0/5 | 0/5 |

In another series of experiments, the primary rat cell lines used for challenging the vaccinated rats are cotransfected with:

1) a plasmid containing the HPV-16 genome under the control of its own promoter, 2) a plasmid coding for a gene for resistance to G418 and for EJ-RAS, which transforms only established cell lines or lines expressing an immortalizing gene. The line RE604 is thereby obtained. Table VI presents the results obtained under these experimental conditions.

TABLE VI

| Challenge by injection of $2 \times 10^4$ RE604 line cells per rat ||||
|---|---|---|---|
| Recombinant virus | Rejection | Delay in the appearance of the tumor | Total |
| VVhE6 | 0/30 | 6/30 | 6/30 |
| VVhE7 | 7/40 | 10/40 | 17/40 |
| VVhE6/VVhE7 | 0/10 | 2/10 | 2/10 |
| VV0 | 0/30 | 0/30 | 0/30 |

The results of these experiments bring out the important part played by the E7 and E6 antigens in protection against the development of tumors induced by HPV-16.

In all the cell lines, the expression of the E7 protein is verified by immunoprecipitation. The protective action exerted by the E7 antigen is hence not dependent on the line under study.

The following strains were deposited on Feb. 24, 1989 at the Collection Nationale de Cultures de Microorganismes (National Collection of Microorganism Cultures) of the Pasteur Institute (Paris):

E. coli pTG2198 under No. I-837.

E. coli pTG2199 under No. I-838.

E. coli pTG3180 under No. I-839.

REFERENCES

1. Treisman, R. Novak, U., Favaloro, J. & Kamen, R. Nature 292, 595–600 (1981).

2. Rassoulzadegan, M., Cowie, A., Carr, A., Glaichenhaus, N., Kamen, R. & Cuzin, F. Nature 300, 713–718 (1982).

3. Lathe, R., Balland, A., Kohli, V. & Lecocq, J. P. Gene 20, 187–195 (1982).

4. Kieny, M. P., Lathe, R., Drillien, R., Sphener, D., Skory, S., Schmitt, D., Wiktor, T. J., Koprowski, H. & Lecocq, J. P. Nature 213, 163–166 (1984).

5. Clertant, P., Gaudray, P., May, E. & Cuzin, F. J. Biol. Chem. 259, 15196–15203 (1984).

6. Takemoto, K. K., Malmgrem, R. A. & Habel, K. Virology 28, 485–488 (1966).

7. Schaffhausen, B. S., Dorai, H., Arakere, G. & Benjamin, T. L. Molec. Cell. Biol. 2, 1187–1198 (1982).

8. Zhu, Z. Veldman, G. M., Cowie, A., Carr, A., Schaffhausen, B. & Kamen, R. J. Virol. 51, 170–180 (1984).

9. Dilworth, S. M., Hansson, H. A., Darnfors, C., Bjursell, G., Streuli, C. H. & Griffin, B. E. Embo, J. 5, 491–499 (1986).

10. Old, L. J., Clarke, D. A. & Benacerraf, B. Nature 184, 291–292 (1959).

11. Binetruy, B. et al. (1982). Embo J. 82, 621–628.

12. Kieny, M. P. et al (1983). Gene 26, 91–99.

13. Kieny, M. P. et al (1984). Nature 312, 163–166.

14. Davis G. et al (1986). Bacis methods in molecular biology (Elsevier).

15. Androphy, E. J. et al (1987) in: The papovaviridae: The papillomaviruses (editors, Salzman, N. P. and Howley, P. M.) Plenum Press, New York, p. 79–85).

16. Schlegel, R. and Wade-Glass, M. (1987) in: The papillomarivuses (editors Salzman), N. P. and Howley, P. M.) Plenum Press, New York, p.87–91.

17. Schiller et al (1984). PNAS 81, 7880.

18. Androphy, E. J. et al. (1986). Science 230, 442–445.
19. Burckhardt, A. et al. (1987). Embo J. 6, 2381–2385.
20. Grisoni, M. et al (1984). Virology 135, 406–416.
21. Lathe, R., et al (1987). Gene 57, 193–201.
22. Androphy, E. J. et al (1987). Embo J. 6, 989–992.
23. Shotkin and Wettstein (1986). PNAS 83, 1689–1694.
24. Storey, A. et al (1988). Embo J. 7, 1815–1820.

We claim:

1. A method of treating tumors using recombinant vaccinia viruses encoding an immunogenic part of a tumor-specific antigen of a virus that induced said tumors, comprising the steps of:
    a) preparing a recombinant vaccinia virus comprising
        i) a heterologous DNA sequence which codes at least for a region essential for inducing an immune response to the tumor-specific antigen and
        ii) regulatory elements required for expression of said DNA sequence in higher cells,
    wherein said heterologous DNA sequence and said regulatory elements are cloned within a non-essential region of said vaccinia virus; and
    b) administering said recombinant vaccinia virus to humans or animals having said tumors.

2. The method of claim 1, wherein said recombinant vaccinia is administered to humans or animals as a pharmaceutical product having a preventive activity against tumors or anti-tumor activity.

3. The method of claim 2, wherein said pharmaceutical product contains a pharmaceutically acceptable vehicle enabling it to be administered by injection into humans or animals.

4. The method of claim 1, wherein said DNA sequence codes for a protein encoded by an oncogenic virus.

5. The method of claim 4, wherein said DNA sequence originates from an oncogenic DNA virus or is a DNA copy from an oncogenic DNA virus.

6. The method of claim 5, wherein said DNA sequence originates from a virus selected from the group consisting of papovaviruses and retroviruses.

7. A method of claim 6, wherein said DNA sequence originates from a papovavirus selected from the group consisting of papillomavirus and polyomaviruses.

8. A method of treating tumors using recombinant vaccinia viruses encoding an immunogenic part of a tumor-specific antigen of a virus that induced said tumors, comprising the steps of:
    a) preparing a recombinant vaccinia virus comprising
        i) a heterologous DNA sequence which codes for at least an essential region of a non-structural protein from a papillomavirus and
        ii) regulatory elements required for expression of said DNA sequence in higher cells,
    wherein said heterologous DNA sequence and said regulatory elements are cloned within a non-essential region of said vaccinia virus; and
    b) administering said recombinant vaccinia virus to humans or animals having said tumors.

9. The method of claim 8, wherein said regulatory elements comprise a transcription promoter and translation initiation and termination signals.

10. The method of claim 9, wherein said transcription promoter originates from said vaccinia virus.

11. The method of claim 10, wherein said promoter is the promoter of the 7.5K protein gene of the vaccinia virus.

12. The method of claim 9, wherein said DNA sequence comprises the translation initiation and termination signals of vaccinia virus.

13. The method of claim 12, wherein said translation initiation signal contains an A or a G in position-3.

14. The method of any of claims 8 to 13, wherein said DNA sequence codes for at least one early protein of the early proteins of an HPV-16 virus.

15. The method of claim 14, wherein said early proteins are selected from the group consisting of E1, E2, E4, E5, E6, and E7.

16. The method of claim 15, wherein said early proteins are selected from the group consisting of E6, E7, and E5.

17. The method of claim 16, wherein said early protein is the E7 protein.

18. The method of claim 16, wherein said early protein is the E5 protein whose coding sequence is shown in FIG. 9.

19. The method of claim 16, wherein said early protein is the E6 protein.

20. The method of claim 14, wherein said DNA sequence is cloned within a thymidine kinase (TK) gene.

21. The method of any of claims 1, 4–6, 8–10 or 15–18, wherein said DNA sequence is cloned within a thymidine kinase (TK) gene.

22. A method of treating tumors using recombinant vaccinia viruses encoding an immunogenic part of a tumor specific antigen of a virus that induced said tumors, comprising the steps of:
    a) preparing a recombinant vaccinia virus comprising:
        i) a heterologous DNA sequence which codes for at least an essential region of a T antigen protein from a polyomavirus, and
        ii) regulatory elements required for expression of said DNA sequence in higher cells,
    wherein said heterologous DNA sequence and said regulatory elements are cloned within a non-essential region of vaccinia virus; and
    b) administering said recombinant vaccinia virus to humans or animals having said tumors.

23. The method of claim 22, wherein said regulatory elements comprise a transcription promoter and translation initiation and termination signals.

24. The method of claim 23, wherein said transcription promoter originates from said vaccinia virus.

25. The method of claim 24 wherein said promoter is the promoter of the 7.5K protein gene of the vaccinia virus.

26. The method of any one of claims 12, 23, 24 or 25, wherein said DNA sequence is cloned within a TK gene.

* * * * *